US011712259B2

(12) United States Patent
Zheng et al.

(10) Patent No.: US 11,712,259 B2
(45) Date of Patent: Aug. 1, 2023

(54) LINEARLY ACTUATABLE CATHETERS, SYSTEMS, AND METHODS

(71) Applicant: C.R. Bard, Inc., Franklin Lakes, NJ (US)

(72) Inventors: Peng Zheng, Chandler, AZ (US); Aseem Singh, Tempe, AZ (US); Deepa Pandia, Gilbert, AZ (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 1041 days.

(21) Appl. No.: 16/348,923

(22) PCT Filed: May 2, 2017

(86) PCT No.: PCT/US2017/030675
§ 371 (c)(1),
(2) Date: May 10, 2019

(87) PCT Pub. No.: WO2018/097856
PCT Pub. Date: May 31, 2018

(65) Prior Publication Data
US 2019/0262016 A1 Aug. 29, 2019

Related U.S. Application Data

(63) Continuation-in-part of application No. 15/360,834, filed on Nov. 23, 2016, now abandoned.

(51) Int. Cl.
*A61B 17/32* (2006.01)
*A61B 17/22* (2006.01)
*A61B 17/00* (2006.01)

(52) U.S. Cl.
CPC ............... *A61B 17/320068* (2013.01); *A61B 17/22012* (2013.01); *A61B 2017/00973* (2013.01);
(Continued)

(58) Field of Classification Search
CPC .......... A61B 17/2202; A61B 17/22004; A61B 17/22012; A61B 17/320068;
(Continued)

(56) References Cited

U.S. PATENT DOCUMENTS 5,163,421 A 11/1992 Bernstein et al.
5,255,669 A 10/1993 Kubota et al.
(Continued)

FOREIGN PATENT DOCUMENTS

CN 101137404 A 3/2008
CN 104042299 A 9/2014
(Continued)

OTHER PUBLICATIONS

Office Action dated Nov. 29, 2021 pertaining to Chinese Patent Application 201780072386.9. (English Translation).
(Continued)

*Primary Examiner* — Jocelin C Tanner
(74) *Attorney, Agent, or Firm* — Dinsmore & Shohl LLP

(57) ABSTRACT

Provided herein is a catheter assembly including, in some embodiments, a core wire configured for linear actuation and a damping mechanism around the core wire. The core wire includes a proximal end with a sonic connector configured to couple to an ultrasound-producing mechanism. The core wire includes a distal end configured to modify intravascular lesions with vibrational energy from the ultrasound-producing mechanism. The damping mechanism includes a gasket system and a retainer to retain the gasket system in a damping-mechanism bore of the catheter assembly. The damping mechanism is around a proximal-end portion of the core wire, where the damping system can provide a compressive force sufficient to dampen transverse wave-producing vibrational energy in the proximal-end portion of the core wire without restricting the linear actuation of the core
(Continued)

Figure 1:
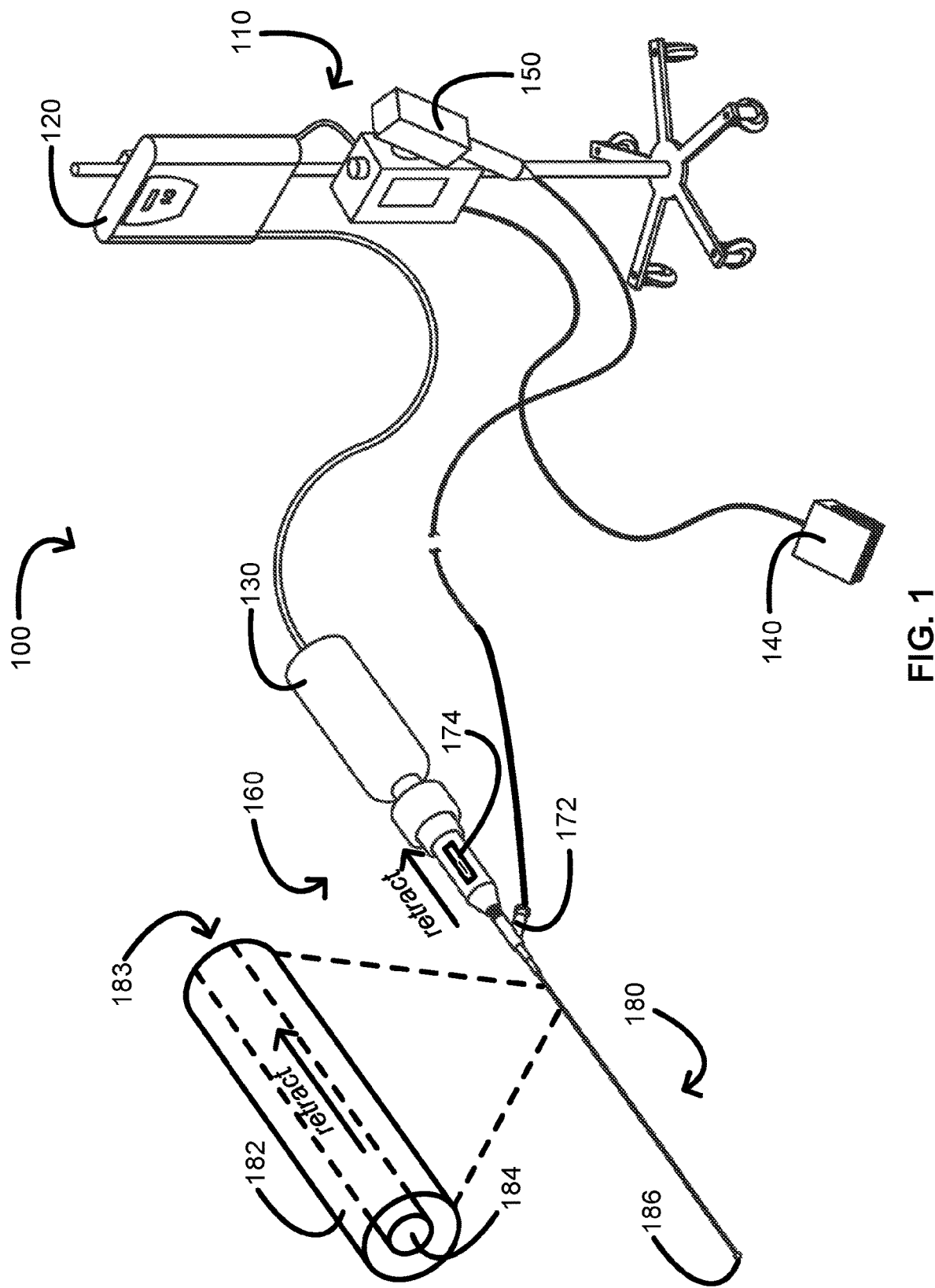

wire through the damping mechanism including extension and retraction of the core wire through the damping mechanism.

12 Claims, 5 Drawing Sheets

(52) U.S. Cl.
CPC ............ *A61B 2017/22014* (2013.01); *A61B 2017/22075* (2013.01); *A61B 2017/320069* (2017.08); *A61B 2017/320072* (2013.01)

(58) Field of Classification Search
CPC ........... A61B 2017/22015; A61B 2017/22014; A61B 2017/00973; A61B 2017/22075; A61B 2017/320069; A61B 2017/320072; A61B 2017/320088; A61B 2090/0807
See application file for complete search history.

(56) References Cited

U.S. PATENT DOCUMENTS

| | | | |
|---|---|---|---|
| 5,312,328 A | 5/1994 | Nita et al. | |
| 5,397,293 A | 3/1995 | Alliger et al. | |
| 5,397,301 A | 3/1995 | Pflueger et al. | |
| 5,916,192 A * | 6/1999 | Nita | A61B 18/245 604/509 |
| 5,989,208 A | 11/1999 | Nita | |
| 5,989,275 A | 11/1999 | Estabrook et al. | |
| 7,131,983 B2 | 11/2006 | Murakami | |
| 8,647,293 B2 * | 2/2014 | Nita | A61B 17/320068 604/528 |
| 2004/0024402 A1 * | 2/2004 | Nita | A61B 17/320068 606/45 |
| 2004/0167507 A1 * | 8/2004 | Nita | A61B 17/22012 606/27 |
| 2013/0072824 A1 * | 3/2013 | Nita | A61B 17/22 601/2 |
| 2013/0345617 A1 * | 12/2013 | Wallace | A61B 17/22004 606/128 |
| 2014/0148833 A1 | 5/2014 | Nita et al. | |
| 2014/0155922 A1 | 6/2014 | Nita | |
| 2015/0039004 A1 * | 2/2015 | Sarge | A61B 17/22012 606/169 |

FOREIGN PATENT DOCUMENTS

| | | |
|---|---|---|
| JP | 6-507081 A | 8/1994 |
| WO | 9211815 A2 | 7/1992 |
| WO | 2016081026 A1 | 5/2016 |
| WO | 2018089197 A1 | 5/2018 |

OTHER PUBLICATIONS

Office Action dated Aug. 31, 2022, pertaining to Japanese Patent Application No. 2019-547570, Appeal 2022-3641.
Office Action dated Oct. 18, 2022, pertaining to European Patent Application 17 874 057.7.

* cited by examiner

LINEARLY ACTUATABLE CATHETERS, SYSTEMS, AND METHODS

CROSS-REFERENCE

This application is a U.S. national phase of International Application No. PCT/US2017/030675, filed May 2, 2017, which claims the benefit of U.S. patent application Ser. No. 15/360,834, filed Nov. 23, 2016, titled "CATHETER WITH RETRACTABLE SHEATH AND METHODS THEREOF," each of which is hereby incorporated herein by reference in its entirety.

BACKGROUND

Atherosclerosis is characterized by one or more intravascular lesions formed, in part, of plaque including blood-borne substances such as fat, cholesterol, and calcium. An intravascular lesion such as an arterial lesion can form on a wall of an arterial lumen and build out across the lumen to an opposite wall thereof. A last point of patency often occurs at a boundary between the arterial lesion and the opposite wall of the arterial lumen. Surgical procedures for atherosclerosis such as angioplasty or atherectomy can be used to restore patency and blood flow lost to the one or more intravascular lesions.

An atherosclerotic surgical procedure can involve advancing one or more endoluminal devices to an intravascular lesion to modify the intravascular lesion. For example, angioplasty or atherectomy can involve advancing an endoluminal device over a guidewire to an intravascular lesion for modification thereof. However, advancing the endoluminal device over the guidewire to the intravascular lesion can lead to surgical complications from device complications, especially in tortuous anatomy where a tip of the endoluminal device can hang up and become derailed from the guidewire. Provided herein in some embodiments are linearly actuatable catheters, systems, and methods that address the foregoing.

SUMMARY

Provided herein is a catheter assembly including, in some embodiments, a core wire configured for linear actuation and a damping mechanism around the core wire configured to dampen vibrational energy. The core wire includes a proximal end with a sonic connector configured to couple to an ultrasound-producing mechanism for imparting vibrational energy to the core wire. The core wire includes a distal end configured to modify intravascular lesions with vibrational energy. The damping mechanism includes a gasket system and a retainer to retain the gasket system in a damping-mechanism bore of the catheter assembly. The damping mechanism is around a proximal-end portion of the core wire, where the damping mechanism is configured to dampen transverse wave-producing vibrational energy in the proximal-end portion of the core wire. The gasket system provides a compressive force sufficient to dampen transverse wave-producing vibrational energy in the proximal-end portion of the core wire without restricting the linear actuation of the core wire through the damping mechanism including extension and retraction of the core wire through the damping mechanism.

In such embodiments, the catheter assembly further includes a linear actuation mechanism configured to extend the core wire from a fully retracted state of the core wire and retract the core wire from a fully extended state of the core wire. In the fully extended state, the distal end of the core wire and a working length of the core wire up to about 20 cm from a distal end of a sheath around the core wire is exposed. In the fully retracted state, the working length of the core wire up to at least the distal end of the core wire is concealed in the sheath.

In such embodiments, a center of the gasket system is positioned over the core wire where the core wire experiences minimal transverse wave-producing vibrational energy, thereby reducing frictional heating and obviating a heat sink.

In such embodiments, the gasket system includes a number of axially and radially compressed O-rings in the damping-mechanism bore providing the compressive force around the core wire. The number of O-rings are axially compressed in the damping-mechanism bore by a distal end of the damping-mechanism bore and the retainer fixed in a proximal end of the damping-mechanism bore. The number of O-rings are radially compressed by an inner wall of the damping-mechanism bore.

In such embodiments, the catheter assembly further includes an injector configured to inject an irrigant into an irrigation port of the catheter assembly. The compressive force around the core wire is further sufficient to prevent irrigation backflow of the irrigant without restricting the extension or retraction of the core wire through the damping mechanism.

In such embodiments, the catheter assembly further includes a polymeric sleeve around an exposed portion of the proximal-end portion of the core wire between the sonic connector and the retainer. The polymeric sleeve is further around the proximal-end portion of the core wire in the damping mechanism, and the polymeric sleeve includes a lubricious surface to facilitate the extension and retraction of the core wire through the damping mechanism.

In such embodiments, the catheter assembly further includes an ultrasound transducer at the proximal end of the core wire forming a portion of an ultrasound-producing mechanism for imparting vibrational energy to the core wire.

Also provided herein is a catheter assembly including, in some embodiments, a linear actuation mechanism, a core wire configured for linear actuation by the linear actuation mechanism, and a damping mechanism around the core wire configured to dampen vibrational energy. The core wire includes a proximal end with a sonic connector configured to accept vibrational energy imparted thereto. The core wire also includes a distal end with a tip member configured to modify intravascular lesions with vibrational energy. The damping mechanism includes a gasket system and a retaining washer to retain the gasket system in a damping-mechanism bore of the catheter assembly. The damping mechanism is around a proximal-end portion of the core wire, where the damping mechanism is configured to dampen transverse wave-producing vibrational energy in the proximal-end portion of the core wire. The gasket system provides a compressive force sufficient to dampen transverse wave-producing vibrational energy in the proximal-end portion of the core wire without restricting the linear actuation of the core wire through the damping mechanism including extension and retraction of the core wire through the damping mechanism.

In such embodiments, the linear actuation mechanism is configured to extend the core wire from a fully retracted state of the core wire and retract the core wire from a fully extended state of the core wire. In the fully extended state, the tip member and a working length of the core wire up to about 20 cm from a distal end of a sheath around the core wire is exposed. In the fully retracted state, the working length of the core wire up to at least the tip member is concealed in the sheath.

In such embodiments, the gasket system includes a number of axially and radially compressed O-rings in the damping-mechanism bore providing the compressive force around the core wire. The compressive force is further sufficient to prevent irrigation backflow of an irrigant without restricting the extension or retraction of the core wire through the damping mechanism. The number of O-rings are axially compressed in the damping-mechanism bore by a distal end of the damping-mechanism bore and the retaining washer fixed in a proximal end of the damping-mechanism bore. The number of O-rings are radially compressed by an inner wall of the damping-mechanism bore.

In such embodiments, the catheter assembly further includes a polymeric sleeve around the proximal-end portion of the core wire in the damping mechanism. The polymeric sleeve includes a lubricious surface to facilitate a full extent of the linear actuation of the core wire through the damping mechanism.

In such embodiments, the catheter assembly further includes an ultrasound transducer at the proximal end of the core wire forming a portion of an ultrasound-producing mechanism for imparting vibrational energy to the core wire.

In such embodiments, the ultrasound transducer is configured for linear actuation by the linear actuation mechanism. The linear actuation of the ultrasound transducer is in sync with the linear actuation of the core wire to maintain a sonic connection between the ultrasound transducer and the core wire through the sonic connector.

Also provided herein is a system including, in some embodiments, a catheter assembly and an ultrasonic energy-producing mechanism. The catheter assembly includes a linear actuation mechanism, a core wire configured for linear actuation by the linear actuation mechanism, and a damping mechanism around the core wire configured to dampen vibrational energy. The core wire includes a proximal end with a sonic connector configured to accept vibrational energy imparted thereto. The core wire also includes a distal end with a tip member configured to modify intravascular lesions with vibrational energy. The damping mechanism includes a gasket system and a retaining washer to retain the gasket system in a damping-mechanism bore of the catheter assembly. The damping mechanism is around a proximal-end portion of the core wire, where the damping mechanism is configured to dampen transverse wave-producing vibrational energy in the proximal-end portion of the core wire. The gasket system provides a compressive force sufficient to dampen transverse wave-producing vibrational energy in the proximal-end portion of the core wire without restricting the linear actuation of the core wire through the damping mechanism including extension and retraction of the core wire through the damping mechanism. The ultrasonic energy-producing mechanism includes an ultrasound generator and an ultrasound transducer. The ultrasound transducer is configured to impart vibrational energy to the sonic connector at the proximal end of the core wire.

In such embodiments, the linear actuation mechanism is configured to extend the core wire from a fully retracted state of the core wire and retract the core wire from a fully extended state of the core wire. In the fully extended state, the tip member and a working length of the core wire up to about 20 cm from a distal end of a sheath around the core wire is exposed. In the fully retracted state, the working length of the core wire up to at least the tip member is concealed in the sheath.

In such embodiments, the gasket system includes a number of axially and radially compressed O-rings in the damping-mechanism bore providing the compressive force around the core wire. The compressive force is further sufficient to prevent irrigation backflow of an irrigant without restricting the extension or retraction of the core wire through the damping mechanism. The number of O-rings are axially compressed in the damping-mechanism bore by a distal end of the damping-mechanism bore and the retaining washer fixed in a proximal end of the damping-mechanism bore. The number of O-rings are radially compressed by an inner wall of the damping-mechanism bore.

In such embodiments, the system further includes a polymeric sleeve around the proximal-end portion of the core wire in the damping mechanism. The polymeric sleeve includes a lubricious surface to facilitate a full extent of the linear actuation of the core wire through the damping mechanism.

In such embodiments, the system further includes a console including a foot switch and the ultrasonic energy-producing mechanism including the ultrasound generator and the ultrasound transducer. The foot switch is configured to activate and deactivate the ultrasonic energy-producing mechanism.

In such embodiments, the system further includes a console including a foot switch and the ultrasound generator of the ultrasonic energy-producing mechanism. The catheter assembly further includes the ultrasound transducer of the ultrasonic energy-producing mechanism. The foot switch is configured to activate and deactivate the ultrasonic energy-producing mechanism.

In such embodiments, the ultrasound transducer is configured for linear actuation by the linear actuation mechanism. The linear actuation of the ultrasound transducer is in sync with the linear actuation of the core wire to maintain a sonic connection between the ultrasound transducer and the core wire through the sonic connector.

Also provided herein is a method including, in some embodiments, molding a cartridge of a catheter assembly and assembling a damping mechanism around a core wire in the cartridge. Molding the cartridge includes molding the cartridge with a damping-mechanism bore. Assembling the damping mechanism around the core wire in the cartridge includes disposing the core wire through a center of the damping-mechanism bore coincident with a rotational axis of the cartridge. A number of O-rings are disposed in the damping-mechanism bore around the core wire, and a washer is fixed in a proximal end of the damping-mechanism bore to form the damping mechanism around the core wire. Fixing the washer in the proximal end of the damping-mechanism bore generates a radial compressive force on the core wire from axially compressing the number of O-rings against a distal end of the damping-mechanism bore. Axially compressing the number of O-rings against the distal end of the damping-mechanism bore, in turn, generates the radial compressive force on the core wire from radially compressing the number of O-rings against an inner wall of the damping-mechanism bore opposing the core wire. The radial compressive force is sufficient to dampen transverse wave-producing vibrational energy imparted to a proximal-end portion of the core wire without restricting linear actuation of the core wire through the damping mechanism.

In such embodiments, the method further includes disposing the core wire in a polymeric sleeve and uniformly heating the polymeric sleeve to shrink the polymeric sleeve around the core wire before disposing the core wire through the center of the damping-mechanism bore. The polymeric sleeve is formed of a lubricious polymer to facilitate a full extent of the linear actuation of the core wire through the damping mechanism.

In such embodiments, the method further includes molding a housing of a catheter assembly; disposing the cartridge with the damping mechanism around the core wire in the housing of the catheter assembly; and connecting the core wire to an linear actuation mechanism of the catheter assembly. Thereby, the core wire of the catheter assembly is configured for the linear actuation through the damping mechanism.

These and other features of the concepts provided herein may be better understood with reference to the drawings, description, and appended claims.

DRAWINGS

FIG. 1 provides a schematic illustrating a system in accordance with some embodiments.

Figure 2A:
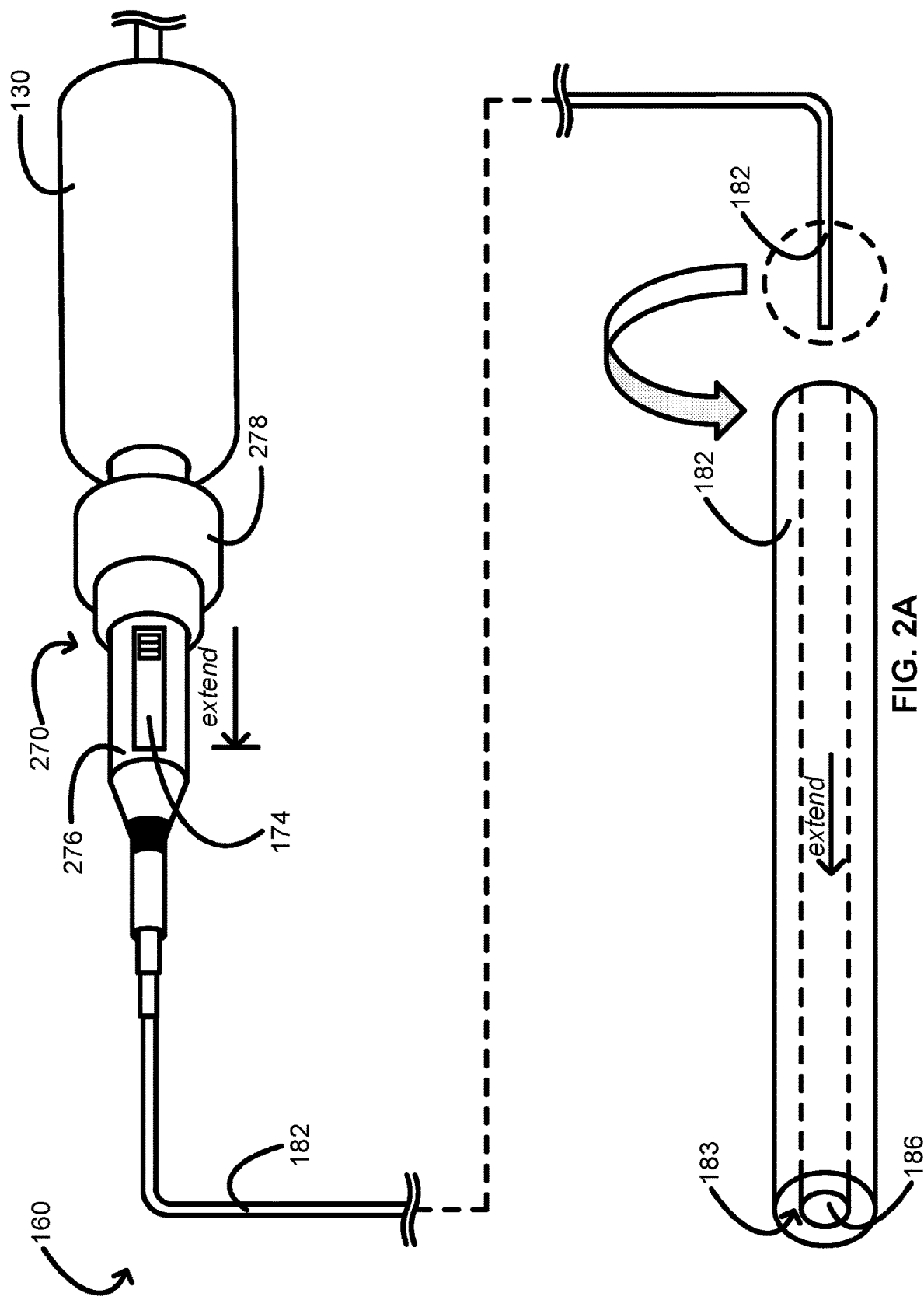

FIG. 2A provides a schematic illustrating a catheter assembly with a linear actuation mechanism configured to extend a core wire from a first, fully retracted state of the core wire in accordance with some embodiments.

Figure 2B:
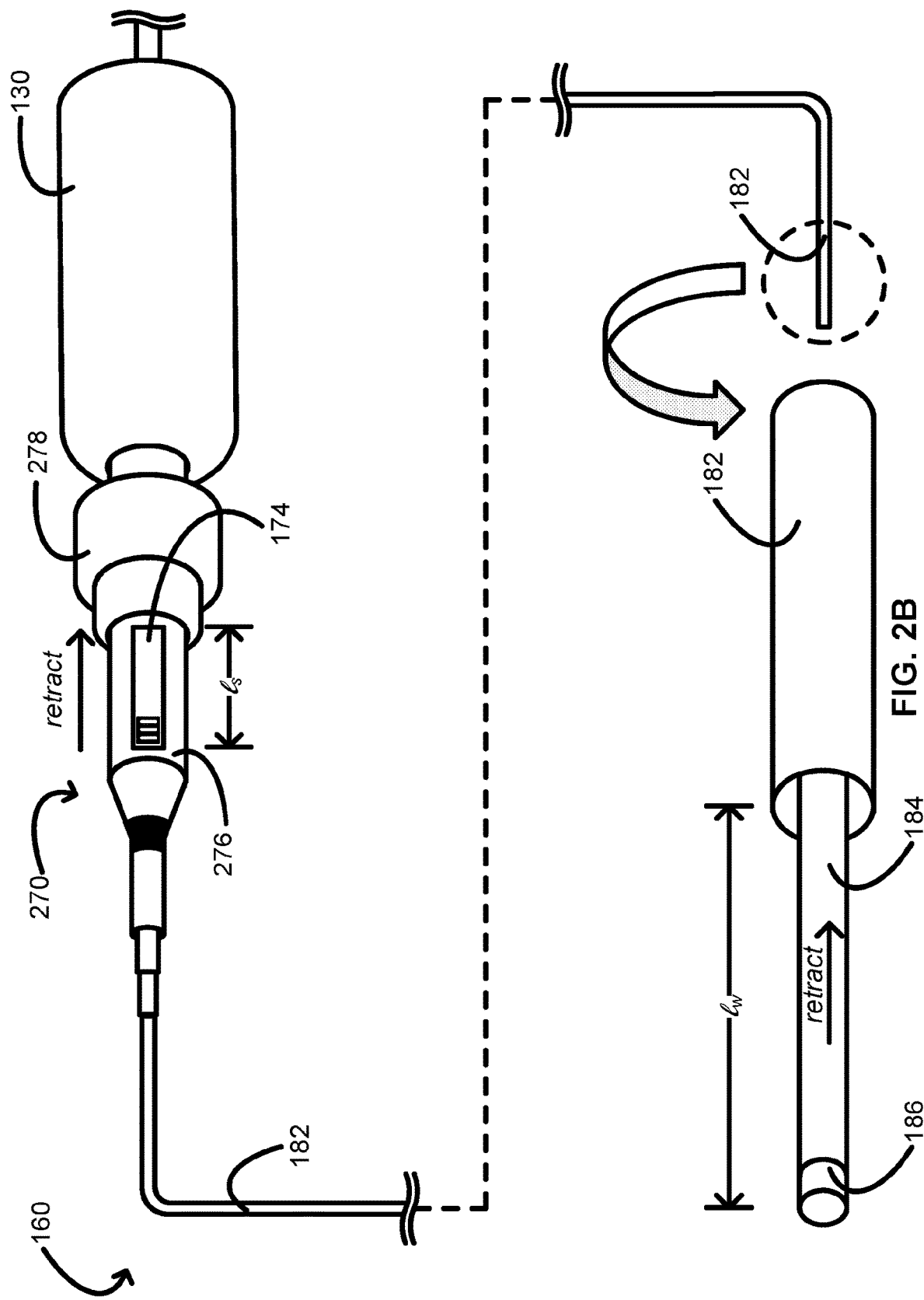

FIG. 2B provides a schematic illustrating a catheter assembly with a linear actuation mechanism configured to retract a core wire from a second, fully extended state of the core wire in accordance with some embodiments.

Figure 3A:
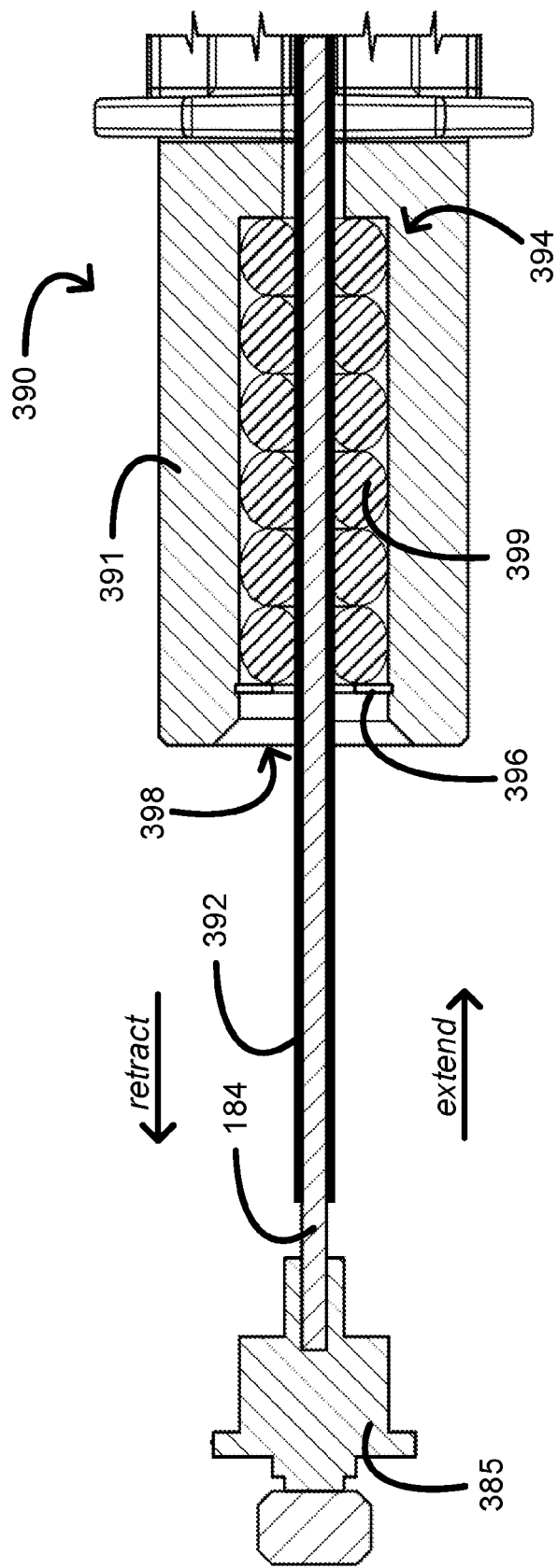

FIG. 3A provides a schematic illustrating a damping mechanism configured for damping and linear actuation of a core wire in accordance with some embodiments.

Figure 3B:
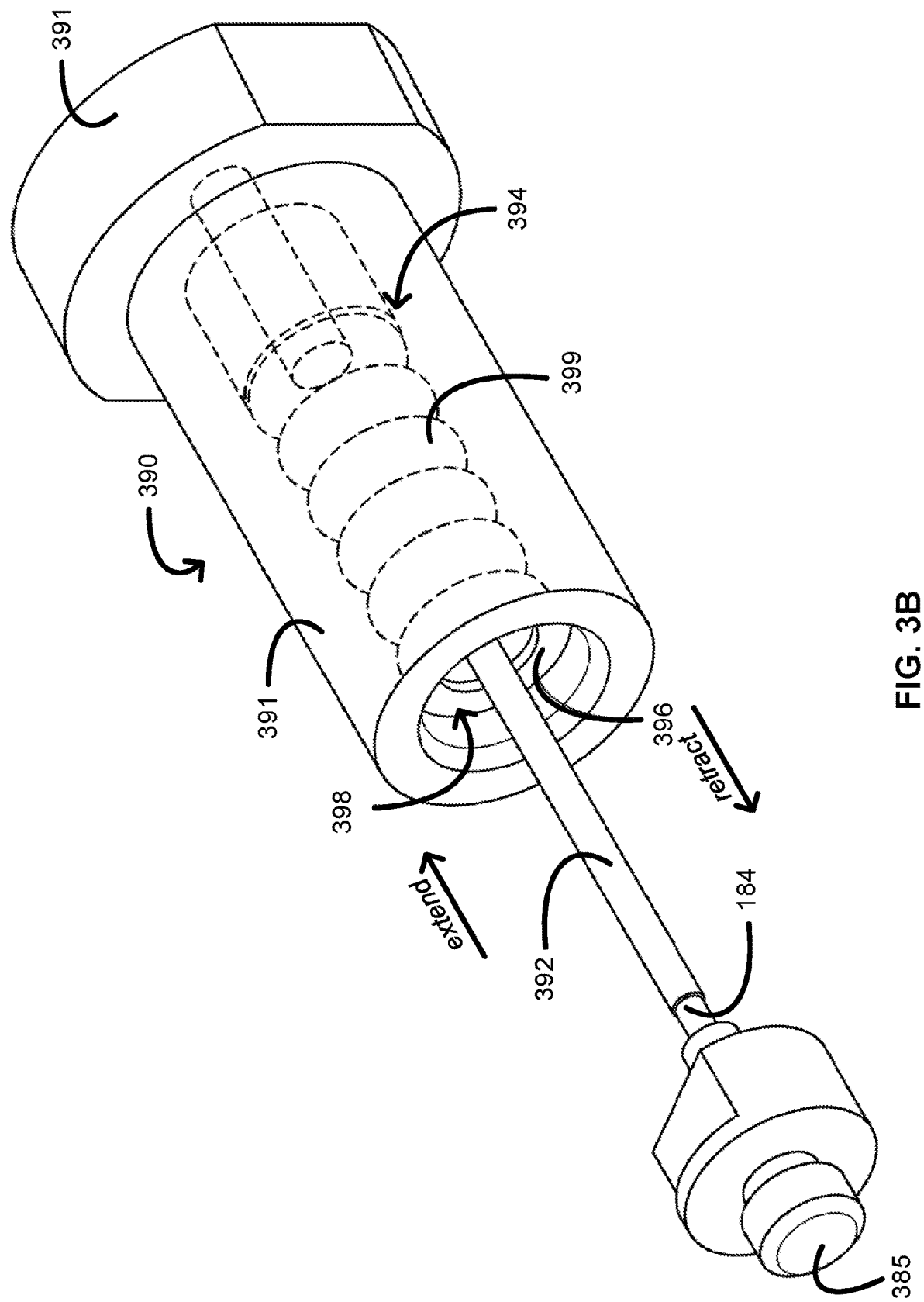

FIG. 3B provides a schematic illustrating a damping mechanism configured for damping and linear actuation of a core wire in accordance with some embodiments.

DESCRIPTION

Before some particular embodiments are provided in greater detail, it should be understood that the particular embodiments provided herein do not limit the scope of the concepts provided herein. It should also be understood that a particular embodiment provided herein can have features that can be readily separated from the particular embodiment and optionally combined with or substituted for features of any of a number of other embodiments provided herein.

Regarding terminology used herein, it should also be understood the terminology is for the purpose of describing some particular embodiments, and the terminology does not limit the scope of the concepts provided herein. Unless indicated otherwise, ordinal numbers (e.g., first, second, third, etc.) are used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

With respect to "proximal," a "proximal portion" or a "proximal-end portion" of, for example, a sheath or core wire respectively includes a portion of the sheath or core wire near a system operator when the system is used as intended. Likewise, a "proximal length" of, for example, the sheath or core wire respectively includes a length of the sheath or core wire near the system operator when the system is used as intended. A "proximal end" of, for example, the sheath or core wire respectively includes an end of the sheath or core wire near the system operator when the system is used as intended. The proximal portion, the proximal-end portion, or the proximal length of the sheath or core wire can include the proximal end of the sheath or core wire; however, the proximal portion, the proximal-end portion, or the proximal length of the sheath or core wire need not include the proximal end of the sheath or core wire. That is, unless context suggests otherwise, the proximal portion, the proximal-end portion, or the proximal length of the sheath or core wire is not a terminal portion or terminal length of the sheath or core wire.

With respect to "distal," a "distal portion" or a "distal-end portion" of, for example, a sheath or core wire respectively includes a portion of the sheath or core wire away from a system operator when the system is used as intended. Likewise, a "distal length" of, for example, the sheath or core wire respectively includes a length of the sheath or core wire away from the system operator when the system is used as intended. A "distal end" of, for example, the sheath or core wire respectively includes an end of the sheath or core wire away from the system operator when the system is used as intended. The distal portion, the distal-end portion, or the distal length of the sheath or core wire can include the distal end of the sheath or core wire; however, the distal portion, the distal-end portion, or the distal length of the sheath or core wire need not include the distal end of the sheath or core wire. That is, unless context suggests otherwise, the distal portion, the distal-end portion, or the distal length of the sheath or core wire is not a terminal portion or terminal length of the sheath or core wire.

Unless defined otherwise, all technical and scientific terms used herein have the same meaning as commonly understood by those of ordinary skill in the art.

An atherosclerotic surgical procedure can involve advancing one or more endoluminal devices to an intravascular lesion to modify the intravascular lesion. For example, angioplasty or atherectomy can involve advancing an endoluminal device over a guidewire to an intravascular lesion for modification thereof. However, advancing the endoluminal device over the guidewire to the intravascular lesion can lead to surgical complications from device complications, especially in tortuous anatomy where a tip of the endoluminal device can hang up and become derailed from the guidewire. Provided herein in some embodiments are linearly actuatable catheters, systems, and methods that address the foregoing.

FIG. 1 provides a schematic illustrating a system 100 in accordance with some embodiments. The system 100 includes a console 110 coupled to a catheter assembly 160 configured for modifying intravascular lesions including crossing the intravascular lesions, ablating the intravascular lesions, or a combination of crossing and ablating the intravascular lesions.

As shown in FIG. 1, the system 100 includes the console 110. The console 110 provides a system operator an instrument for monitoring and controlling the system 100 and various sub-systems and functions thereof. The console 110 includes an ultrasonic energy-producing mechanism including an ultrasound generator 120 and an ultrasound transducer 130. Alternatively, the console 110 includes the ultrasound generator 120, the catheter assembly 160 includes the ultrasound transducer 130, and the ultrasonic energy-producing mechanism is divided between the console 110 and the catheter assembly 160. The ultrasonic energy-producing mechanism is configured to convert an electric current into a vibrational energy. For example, the ultrasound generator 120 is configured to convert an alternating electric current (e.g., a current associated with mains electricity) into a high-frequency current (e.g., a current with a frequency commensurate with the operating frequency of the ultrasound transducer 130), and the ultrasound transducer 130, in turn, is configured to convert the high-frequency current into the vibrational energy (e.g., >20 kHz such as 20.5 kHz±500 Hz).

The console 110 optionally further include a foot switch 140 configured to activate and deactivate the system 100 such as activate and deactivate a core wire 184 (e.g., a nitinol core wire) of the catheter assembly 160. The core wire 184 is disposed in a core-wire lumen 183 of a sheath 182 of the catheter assembly 160. A proximal end of the core wire 184 is vibrationally coupled to the ultrasound transducer 130, and a distal end of the core wire 184 is vibrationally coupled to a lesion-modifying tip member 186 or a lesion-modifying tip 186 is fashioned from the distal end of the core wire 184. As such, the core wire 184 is configured to transfer the vibrational energy from the ultrasound transducer 130 to the tip member or tip 186 for modifying intravascular lesions. When the system 100 is powered on but not activated, the foot switch 140 is used to activate the system 100, thereby activating the ultrasound transducer 130, the core wire 184, and the tip member or tip 186 of the catheter assembly 160. When the system 100 is powered on and activated, the foot switch 140 is used to deactivate the system 100, thereby deactivating the ultrasound transducer 130, the core wire 184, and the tip member or tip 186 of the catheter assembly 160.

The console 110 optionally further include an injector 150 configured to inject an irrigant into an irrigation port 172 of the catheter assembly 160. The irrigant includes, for example, a sterile liquid (e.g., water, saline, heparinized saline, etc.) for irrigating an anatomical area undergoing an intravascular lesion-modification procedure (e.g., crossing an intravascular lesion, ablating an intravascular lesion, etc.), cooling the core wire 184 of the catheter assembly 160, or a combination thereof.

The console 110 optionally further include both the foot switch 140 and the injector 150. In such embodiments, the foot switch 140 is further configured to activate and deactivate the injector 150 when the system 100 is respectively activated and deactivated with the foot switch 140.

FIG. 2A provides a schematic illustrating the catheter assembly 160 with an extension-retraction mechanism or linear actuation mechanism 174 configured to extend the core wire 184 from a first, fully retracted position or state of the core wire 184 in accordance with some embodiments. FIG. 2B provides a schematic illustrating the catheter assembly 160 with the extension-retraction mechanism or linear actuation mechanism 174 configured to retract the core wire 184 from a second, fully extended position or state of the core wire 184 in accordance with some embodiments. The catheter assembly 160 includes a housing 270 coupled to a catheter body 180 (see FIG. 1) including the sheath 182 and core wire 184 configured for modifying intravascular lesions including crossing the intravascular lesions, ablating the intravascular lesions, or a combination of crossing and ablating the intravascular lesions.

As shown in FIGS. 2A and 2B, the housing 270 includes a hub 276 and a lock collar 278 for locking the housing 270 onto the ultrasound transducer 130. (The irrigation port 172 is not shown in FIGS. 2A and 2B, as the irrigation port 172 is optional in some embodiments.) Locking the housing 270 onto the ultrasound transducer 130 ensures the proximal end of the core wire 184 is sufficiently vibrationally coupled to the ultrasound transducer 130 for modifying intravascular lesions. Again, the catheter assembly 160 alternatively includes the ultrasound transducer 130, which divides the ultrasonic energy-producing mechanism between the console 110 and the catheter assembly 160. In such embodiments, the housing 270 further includes the ultrasound transducer 130 disposed therein at the proximal end of the core wire, thereby obviating the lock collar 276 shown in FIGS. 2A and 2B. Further in such embodiments, the ultrasound transducer 130 is configured for linear actuation by the linear actuation mechanism 174. The linear actuation of the ultrasound transducer 130 is in sync with the linear actuation of the core wire 184 to maintain a sonic connection between the ultrasound transducer 130 and the core wire 184 through sonic connector 385. (See FIGS. 3A and 3B for the sonic connector 385.)

The linear actuation mechanism 174 is configured to extend the core wire 184 from the first, fully retracted position or state of the core wire 184 as shown in FIG. 2A. In the fully retracted state of the core wire 184, the distal portion of the core wire 184 including the tip member or tip 186 is wholly disposed within the sheath lumen 183. Alternatively, in the fully retracted state of the core wire 184, the tip member or tip 186 is exposed and a remaining distal portion of the core wire 184 is wholly disposed within the sheath lumen 183. The linear actuation mechanism 174 is further configured to retract the core wire 184 from the second, fully extended position or state of the core wire 184 as shown in FIG. 2B. In the fully extended state of the core wire 184, a maximum working length $l_{w(max)}$ of the core wire 184 including the tip member or tip 186 is exposed outside the sheath lumen 183.

It should be understood that the linear actuation mechanism 174 is configured to extend the core wire 184 in a distal direction and retract the core wire 184 in a proximal direction. Furthermore, the linear actuation mechanism 174 is configured to linearly actuate the core wire 184 itself as opposed to any other wire for any other motion of the core wire 184 (e.g., a pulling wire for articulation such as deflection of the core wire 184 through an angle).

As shown in FIGS. 2A and 2B, the housing 270 is configured to accommodate a proximal length of the core wire 184, and the linear actuation mechanism 174 is configured to extend the proximal length of the core wire 184 from the housing 270 and expose a working length $l_w$ of the distal portion of the core wire 184 for ultrasound-based modification of one or more intravascular lesions with the working length $l_w$ of the core wire 184. A maximum working length $l_{w(max)}$ of the core wire 184 is defined by an extension distance over which a point on the core wire 184 extends from the first, fully retracted state to the second, fully extended state. The maximum working length $l_{w(max)}$ of the core wire 184 is also be defined by a slot length is in the housing 270 configured to accommodate the proximal length of the core wire 184 in the first state. The working length $l_w$ of the core wire 184 ranges between about 5 and 200 mm, including between about 5 and 100 mm or between about 100 and 200 mm; however the working length $l_w$, of the core wire 184 is not limited thereto. It should be appreciated that shorter working lengths $l_w$ and smaller catheter-body profiles have benefits in certain instances, whereas longer working lengths $l_w$ and larger catheter-body profiles have benefits in certain other instances (e.g., larger patients).

The linear actuation mechanism 174 is hand actuated as shown in FIGS. 2A and 2B, or the linear actuation mechanism 174 is motor actuated. Whether hand actuated or motor actuated, the linear actuation mechanism 174 is configured to i) extend the core wire 184 from the first, fully retracted state of the core wire 184, ii) retract the core wire 184 from the second, fully extended state of the core wire 184, iii) extend or retract the core wire 184 into intermediate positions or states between the first state and the second state, or iv) any combination thereof. Extension and retraction of the core wire 184 into the foregoing intermediate positions provides customizability as needed for different anatomy and intravascular lesions.

The working length $l_w$ of the distal portion of the core wire 184 beyond the sheath 182 or the sheath lumen 183 thereof is configured for displacement to effect intravascular lesion modification. The displacement includes longitudinal, transverse, or longitudinal and transverse displacement in accordance with a profile of the core wire 184 and the vibrational energy (e.g., >20 kHz such as 20.5 kHz±500 Hz). Longitudinal displacement of the working length $l_w$ of the core wire 184 results in micromotion such as cavitation, and transverse displacement of the working length/w of the core wire 184 results in macromotion. The micromotion is used to cross intravascular lesions. The macromotion coupled with the micromotion is used to ablate intravascular lesions, thereby breaking the lesions into minute fragments and restoring patency and blood flow.

FIGS. 3A and 3B provide schematics illustrating a damping mechanism 390 configured for both damping vibrational energy in the core wire 184 and linear actuation of the core wire 184 therethrough in accordance with some embodiments.

The core wire 184 includes a sonic connector 385 at a proximal end of the core wire 184 configured to connect to an ultrasound-producing mechanism for imparting vibrational energy to the core wire for ultrasound-based modification of one or more intravascular lesions with the working length $l_w$ of the core wire 184. The sonic connector 385 is configured to connect to the ultrasound-producing mechanism by the ultrasound transducer 130 or an intervening ultrasonic horn (not shown). The distal end of the core wire 184 is vibrationally coupled to the lesion-modifying tip member 186 or the lesion-modifying tip 186 is fashioned from the distal end of the core wire 184 for ultrasound-based modification of one or more intravascular lesions.

The catheter assembly 160 includes the damping mechanism 390 about the proximal-end portion of the core wire 184 configured to dampen transverse wave-producing vibrational energy about the proximal-end portion of the core wire 184 in favor of longitudinal wave-producing vibrational energy without restricting the extension or retraction of the core wire 184 through the damping mechanism 390. The damping mechanism 390 includes a gasket system 394 configured to exert a compressive force around the core wire 184 and a retainer 396 configured to retain the gasket system 394 within a damping-mechanism bore 398 of a cartridge 391 of the catheter assembly 160.

The gasket system 394 includes a number of O-rings 399. The number of O-rings 399 range from 1 O-ring to 12 O-rings, including 2 O-rings, such as 4 O-rings, for example, 6 O-rings. The number of O-rings 399 are axially compressed in the damping-mechanism bore 398 of the cartridge 391 and retained in the damping-mechanism bore 398 by the retainer 396 (e.g., a washer such as a retaining washer, for example, an external star washer). Axial compression of the number of O-rings 399 generates a radial compression on the core wire 184 sufficient to dampen the transverse wave-producing vibrational energy in favor of the longitudinal wave-producing vibrational energy about the proximal portion of the core wire 184.

The damping mechanism 390 further includes a sleeve 392 around the core wire 184. (Alternatively, the sleeve 392 is considered a part of the linear actuation mechanism 174 in that it facilitates the extension and retraction of the core wire 184 through the damping mechanism 390.) The sleeve 392 is around at least the proximal-end portion of the core wire 184 between the sonic connector 385 and the retainer 398. If not encased by the sleeve 392, the core wire 184 would include an exposed portion of the proximal-end portion of the core wire 184 between the sonic connector 385 and the retainer 398. The sleeve 392 around the proximal-end portion of the core wire 184 between the sonic connector 385 and the retainer 398 prevents fatigue of the core wire 184 therebetween. The sleeve 392 is further around at least the proximal-end portion of the core wire 184 in the damping mechanism 390, as well as around the core wire 184 distal to the damping mechanism 390 up to at least a length commensurate with the working length $l_w$ of the core wire 184. Not only does the sleeve 392 prevent fatigue of the core wire 184, the sleeve 392 also facilitates the extension and retraction of the core wire 184 through the damping mechanism 390. The sleeve 392 includes or otherwise be formed of a polymer providing a relatively lubricious surface that facilitates the extension and retraction of the core wire 392 through the damping mechanism 390.

The sleeve 392 around the core wire 184 encases the core wire 184 with an engineering fit selected from a clearance fit, a transition fit, and an interference fit. The clearance fit is a fairly loose fit that enables the core wire 184 to freely rotate or slide within the sleeve 392; the transition fit firmly holds the core wire 184 in place within the sleeve 392, but not so firmly that the core wire 184 cannot be removed from the sleeve 392; and the interference fit securely holds the core wire 184 in place within the sleeve 392 such that the core wire 184 cannot be removed from the sleeve 392 without damaging the core wire 184, the sleeve 392, or both. In some embodiments, the sleeve 392 encases the core wire 184 with a transition fit or an interference fit. The transition fit and the interference fit are effected by, for example, heat-shrinking a suitably sized sleeve for the desired fit about the core wire 184 during assembly of the catheter assembly 160. The sleeve 392 around the core wire 184 is a polymeric sleeve such as a polytetrafluoroethylene ("PTFE") sleeve.

The damping mechanism 390 is centered over or a vibrational node of the core wire 184, or the core wire 184 can be adjusted such that the damping mechanism 390 is over or a vibrational node of the core wire 184. This minimizes frictional heating caused by damping the transverse wave-producing vibrational energy, and, thereby, obviates a need for a heat sink in the damping mechanism 390 of the catheter assembly 160. In embodiments of the system 100 including the injector 150, the gasket system 394 prevents irrigation backflow of the irrigant through the catheter assembly 160 such as through the damping mechanism 390 and into the ultrasound transducer 130 of the ultrasound-producing mechanism. The gasket system 394 further prevents the irrigation backflow without restricting the extension or retraction of the core wire 184 through the damping mechanism 390.

Making the damping mechanism 390 configured for both damping vibrational energy in the core wire 184 and linear actuation of the core wire 184 therethrough includes molding the cartridge 391 of the catheter assembly 160 and subsequently assembling the damping mechanism 390 around the core wire 184 in the cartridge 391.

Molding the cartridge 391 includes molding the cartridge 391 with a damping-mechanism bore 398. Such molding includes, but is not limited to, compression molding, injection molding, thermoforming, or a combination thereof.

Assembling the damping mechanism 391 around the core wire 184 in the cartridge 391 includes disposing the core wire 184 through a center of the damping-mechanism bore 398 coincident with a rotational axis of the cartridge 391. Prior to disposing the core wire 184 through the center of the damping-mechanism bore 398, the core wire 184 is disposed in a heat-shrinkable polymeric sleeve and uniformly heated to shrink the heat-shrinkable polymeric sleeve around the core wire 184 to form the polymeric sleeve 392 around the core wire 184. The polymeric sleeve 392 is formed of a lubricious polymer (e.g., PTFE) to facilitate a full extent of the linear actuation (i.e., linear actuation from the first, fully retracted state to the second, fully extended state and back again) of the core wire 184 through the damping mechanism 390.

Assembling the damping mechanism 390 around the core wire 184 in the cartridge 391 further includes disposing the number of O-rings 399 in the damping-mechanism bore 398 around the core wire 184, as well as fixing the retainer 396 (e.g., an external star washer) in a proximal end of the damping-mechanism bore 398 to form the damping mechanism 390 around the core wire 184. Fixing the retainer 396 in the proximal end of the damping-mechanism bore 398 generates a radial compressive force on the core wire 184. The radial compressive force occurs from an axial compressive force on the number of O-rings 399 resulting from axially pressing the number of O-rings 399 against a distal end of the damping-mechanism bore 398 with the retainer 396 in the proximal end of the damping-mechanism bore 398. The axial compressive force, in turn, generates the radial compressive force on the core wire 184 via radial expansion of the number of O-rings 399, thereby, radially pressing the number of O-rings 399 against an inner wall of the damping-mechanism bore 398 opposing the core wire 184 and the core wire 184 itself. The radial compressive force is sufficient to dampen transverse wave-producing vibrational energy imparted to the proximal-end portion of the core wire 184 without restricting the linear actuation of the core wire 184 through the damping mechanism 390.

Making the catheter assembly 160 includes molding a housing of the catheter assembly 160, and subsequently disposing the cartridge 391 including the damping mechanism 390 around the core wire 184 in the housing to form the catheter assembly 160. Disposing the cartridge 391 in the housing includes connecting the core wire 184 to the linear actuation mechanism 174 of the catheter assembly 160. Thereby, the core wire 184 of the catheter assembly 160 is configured for the linear actuation through the damping mechanism 390.

While some particular embodiments have been provided herein, and while the particular embodiments have been provided in some detail, it is not the intention for the particular embodiments to limit the scope of the concepts presented herein. Additional adaptations and/or modifications can appear to those of ordinary skill in the art, and, in broader aspects, these adaptations and/or modifications are encompassed as well. Accordingly, departures may be made from the particular embodiments provided herein without departing from the scope of the concepts provided herein.

What is claimed is:

1. A catheter assembly, comprising:
   a core wire configured for linear actuation including extension and retraction, wherein:
      a proximal end of the core wire includes a sonic connector configured to couple to an ultrasound-producing mechanism for imparting vibrational energy to the core wire, and
      a distal end of the core wire is configured to modify intravascular lesions with vibrational energy;
   a damping mechanism around a proximal-end portion of the core wire configured to dampen transverse wave-producing vibrational energy in the proximal-end portion of the core wire, the damping mechanism including:
      a gasket system having a number of axially and radially compressed O-rings in the damping-mechanism bore configured to exert a compressive force around the core wire; and
      a retainer to retain the gasket system in a damping-mechanism bore of the catheter assembly, wherein the compressive force is sufficient to dampen transverse wave-producing vibrational energy in the proximal-end portion of the core wire without restricting the extension or retraction of the core wire through the damping mechanism;
   wherein the O-rings are axially compressed in the damping-mechanism bore by a distal end of the damping-mechanism bore and the retainer fixed in a proximal end of the damping-mechanism bore, and radially compressed by an inner wall of the damping-mechanism bore; and
   a linear actuation mechanism configured to:
      extend the core wire from a fully retracted state of the core wire, and
      retract the core wire from a fully extended state of the core wire, wherein:
         the distal end of the core wire and a working length of the core wire up to about 20 cm from a distal end of a sheath around the core wire are exposed in the fully extended state, and
         the working length of the core wire up to at least the distal end of the core wire are concealed in the sheath in the fully retracted state.

2. The catheter assembly of claim 1, wherein a center of the gasket system is positioned over the core wire where the core wire experiences minimal transverse wave-producing vibrational energy, thereby reducing frictional heating and obviating a heat sink.

3. The catheter assembly of claim 1, further comprising:
   an injector configured to inject an irrigant into an irrigation port of the catheter assembly, wherein the compressive force around the core wire is further sufficient to prevent irrigation backflow of the irrigant without restricting the extension or retraction of the core wire through the damping mechanism.

4. The catheter assembly of claim 1, further comprising:
a polymeric sleeve around an exposed portion of the proximal-end portion of the core wire between the sonic connector and the retainer.

5. The catheter assembly of claim 4, wherein:
the polymeric sleeve is further around the proximal-end portion of the core wire in the damping mechanism, and
the polymeric sleeve includes a lubricious surface to facilitate the extension and retraction of the core wire through the damping mechanism.

6. The catheter assembly of claim 1, further comprising:
an ultrasound transducer at the proximal end of the core wire forming a portion of an ultrasound-producing mechanism for imparting vibrational energy to the core wire.

7. A system, comprising:
a catheter assembly including:
  a core wire configured for linear actuation by a linear actuation mechanism, the linear actuation mechanism configured to:
    extend the core wire from a fully retracted state of the core wire, and
    retract the core wire from a fully extended state of the core wire,
  a tip member and a working length of the core wire up to about 20 cm from a distal end of a sheath around the core wire are exposed in the fully extended state, and
  the working length of the core wire up to at least the tip member are concealed in the sheath in the fully retracted state; and
  wherein a proximal end of the core wire includes a sonic connector configured to accept vibrational energy imparted thereto, and
  a distal end of the core wire includes the tip member, the tip member configured to modify intravascular lesions with vibrational energy; and
a damping mechanism around a proximal-end portion of the core wire configured to dampen transverse wave-producing vibrational energy in the proximal-end portion of the core wire, wherein the damping mechanism includes:
  a gasket system that includes a number of axially and radially compressed O-rings in the damping-mechanism bore configured to exert a compressive force around the core wire; and
  a retaining washer to retain the gasket system in a damping-mechanism bore of the catheter assembly, wherein the compressive force is sufficient to dampen transverse wave-producing vibrational energy in the proximal-end portion of the core wire without restricting the linear actuation of the core wire through damping mechanism; and
  the number of O-rings are axially compressed in the damping-mechanism bore by a distal end of the damping-mechanism bore and the retaining washer fixed in a proximal end of the damping-mechanism bore, and the number of O-rings are radially compressed by an inner wall of the damping-mechanism bore; and
an ultrasonic energy-producing mechanism including:
  an ultrasound generator; and
  an ultrasound transducer, wherein the ultrasound transducer is configured to impart vibrational energy to the sonic connector at the proximal end of the core wire.

8. The system of claim 7, wherein:
the compressive force is further sufficient to prevent irrigation backflow of an irrigant without restricting the extension or retraction of the core wire through the damping mechanism.

9. The system of claim 7, further comprising:
a polymeric sleeve around the proximal-end portion of the core wire in the damping mechanism, wherein the polymeric sleeve includes a lubricious surface to facilitate a full extent of the linear actuation of the core wire through the damping mechanism.

10. The system of claim 7, further comprising:
a console including a foot switch and the ultrasonic energy-producing mechanism including the ultrasound generator and the ultrasound transducer, wherein the foot switch is configured to activate and deactivate the ultrasonic energy-producing mechanism.

11. The system of claim 7, further comprising:
a console including a foot switch and the ultrasound generator of the ultrasonic energy-producing mechanism, wherein:
  the catheter assembly further includes the ultrasound transducer of the ultrasonic energy-producing mechanism, and
  the foot switch is configured to activate and deactivate the ultrasonic energy-producing mechanism.

12. The system of claim 11, wherein:
the ultrasound transducer is configured for linear actuation by the linear actuation mechanism, and
the linear actuation of the ultrasound transducer is in sync with the linear actuation of the core wire to maintain a sonic connection between the ultrasound transducer and the core wire through the sonic connector.

* * * * *